US00PP13862P39

(12) United States Plant Patent
Bessho

(10) Patent No.: US PP13,862 P3
(45) Date of Patent: Jun. 3, 2003

(54) PETUNIA PLANT NAMED 'KAKEGAWA S30'

(75) Inventor: Masao Bessho, Kakegawa (JP)

(73) Assignee: Sakata Seed Corporation, Yokohama (JP)

( * ) Notice: Subject to any disclaimer, the term of this patent is extended or adjusted under 35 U.S.C. 154(b) by 0 days.

(21) Appl. No.: 09/946,090

(22) Filed: Sep. 4, 2001

(65) Prior Publication Data

US 2003/0070197 P1 Apr. 10, 2003

(51) Int. Cl.[7] ..... A01H 5/00
(52) U.S. Cl. ..... Plt./356

(58) Field of Search ..... Plt./356

(56) References Cited

PUBLICATIONS

UPOV–ROM GTITM Computer Database, 2001/06, GTI Jouve Retrieval Software, citation for 'Kakegawa S30'.*

* cited by examiner

*Primary Examiner*—Bruce R. Campell
*Assistant Examiner*—Susan B. McCormick
(74) *Attorney, Agent, or Firm*—Jondle & Associates PC

(57) ABSTRACT

A Petunia plant particularly distinguished by its white flower color and creeping, mounding habit.

1 Drawing Sheet

GENUS AND SPECIES

*Petunia hybrida.*

VARIETY DENOMINATION

'Kakegawa S30'.

BACKGROUND OF THE NEW PLANT

The present invention comprises a new and distinct cultivar of Petunia, botanically known as *Petunia hybrida,* and hereinafter referred to by the cultivar name 'Kakegawa S30'. 'Kakegawa S30' originated from a hybridization made in 1997 in Kakegawa, Japan. The male parent was a phenotypically fixed $F_3$ selection from a cross made in 1994 between two breeding lines, 4UK-1 and P-1a. The female parent of 'Kakegawa S30' was an $F_5$ selection known as 4-966-1a-1, originating from a dwarf multiflora breeding gene pool. $F_1$ seed was obtained from this cross in 1997.

Two hundred $F_1$ plants from the 1997 cross were transplanted to a field in Salinas, Calif. during the summer of 1998. Three lines were selected and vegetatively propagated for further evaluation. The three lines were propagated again in 1999, and evaluated for fixed characteristics and ease of propagation. Final selection of one line from the three was made during the summer of 1999. The line was established as 'Kakegawa S30', and determined to have its characteristics firmly fixed.

The terminal 1.0 to 1.5 inches of an actively growing stem was excised. The vegetative cuttings were propagated in five to six weeks. The base of the cuttings were dipped for 1 to 2 seconds in a 1:9 solution of Dip 'n Grow® (1 solution: 9 water) root inducing solution immediately prior to sticking into the cell trays. Cuttings were stuck into plastic cell trays having 98 cells, and containing a moistened peat moss-based growing medium. The cuttings were misted with water from overhead for 10 seconds every 30 minutes until sufficient roots were formed.

'Kakegawa S30' has been found to retain its distinctive characteristics after two years and four cycles of vegetative propagation and this novelty is firmly fixed. The variety has demonstrated stability during this time and has no inherent variation or off-types.

DESCRIPTION OF PHOTOGRAPH

This new Petunia plant is illustrated by the accompanying photograph which shows blooms, and foliage of the plant in full color, the colors shown being as true as can be reasonably obtained by conventional photographic procedures.

DESCRIPTION OF THE NEW CULTIVAR

Figure 1:
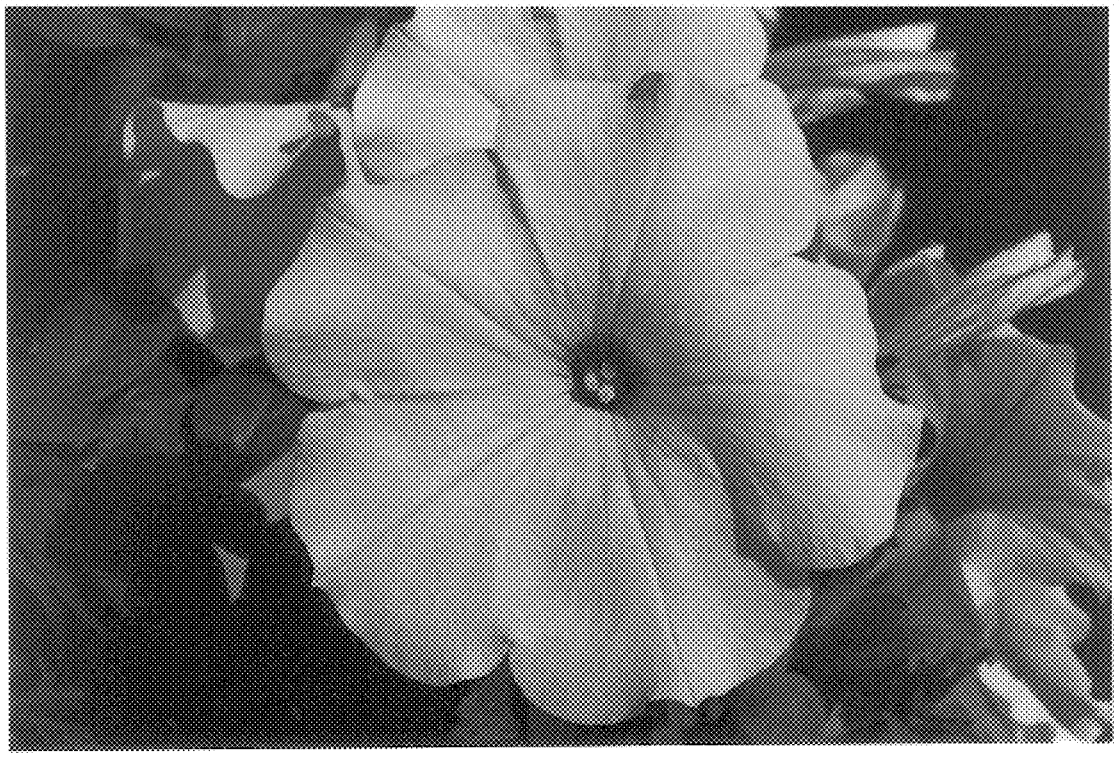
FIG. 1 shows the mature inflorescence.
Figure 2:
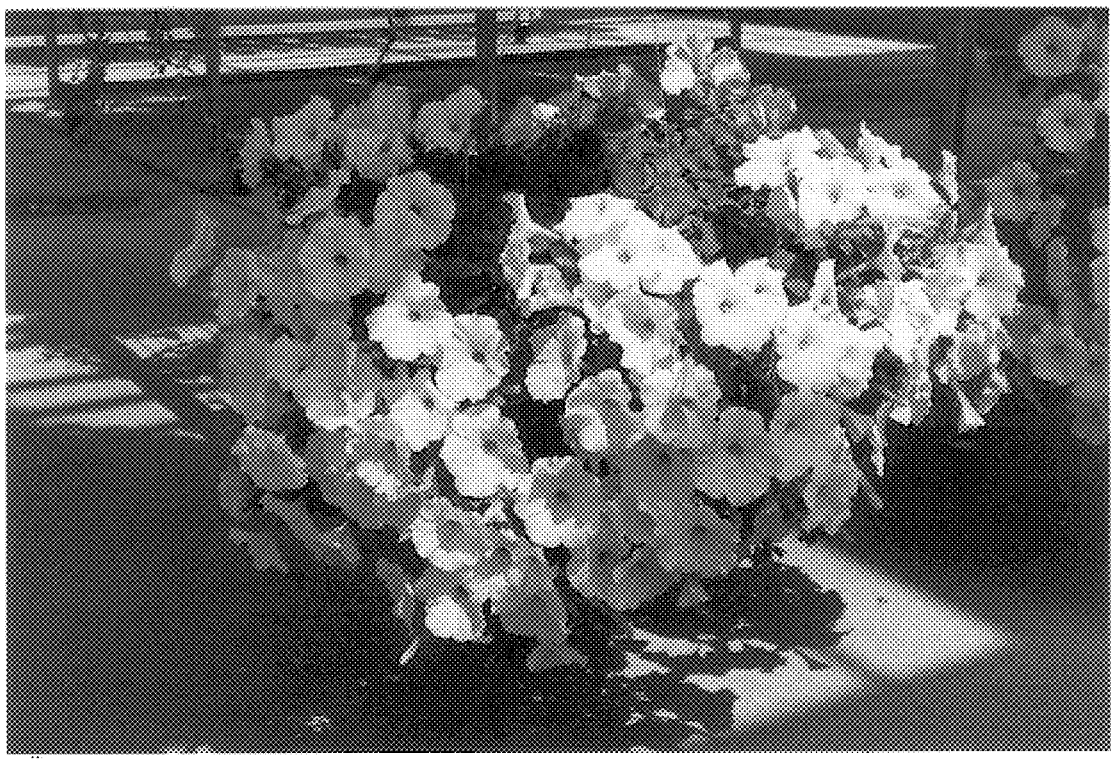
FIG. 2 shows the entire plant approximately eight weeks after transplanting a rooted cutting.

The following detailed descriptions set forth the distinctive characteristics of 'Kakegawa S30'. The data which defines these characteristics were collected from asexual reproductions carried out in Salinas, Calif. Three plants from fully rooted 15 cm diameter pots were transplanted to one 50 cm diameter hanging baskets and grown in the same conditions. Data was collected on plants in 50 cm diameter pots eight weeks after rooted cuttings were transplanted. Color references are primarily to The R.H.S. Colour Chart of The Royal Horticultural Society of London (R.H.S.).

DESCRIPTION OF THE NEW PLANT

Classification:

*Botanical.*—*Petunia hybrida.*

*Commercial.*—Petunia.

Parentage:

*Female parent.*—Breeding line 4-966-1a-1.

*Male parent.*—An $F_3$ selection from the cross of breeding lines 4UK-1 and P-1a.

Environmental conditions for plant growth: Plants were propagated from vegetative cuttings, and grown individually in 15 cm diameter plastic pots in a glass greenhouse located in Salinas, Calif. Pots contained a peat moss-based growing medium. Soluble fertilizer containing 18% nitrogen, 8% phosphorus and 18% potassium was applied in four, daily irrigations. The fifth irrigation was made with non-fertilized water. Pots were top-dressed with a slow release fertilizer containing 18% nitrogen, 8% phosphorus and 18% potassium. The typical average air temperature was 24C. The average time to initiate root development is 7 days after sticking cuttings.

Growth:

*Habit.*—Branching, mounding.

*Form.*—Descending.

*Plant size.*—91 cm total diameter and 76 cm total height when three plants are grown in a 50 cm diameter hanging basket.

*Flowering habit.*—Indeterminate.

*Time to bloom from propagation.*—4–6 weeks after rooting when grown in 10–15 cm diameter plastic pots.

*Life cycle.*—Annual.

Stems:

*Color.*—Yellow-green (RHS 145A).

*Description.*—Round, pubescent.

*Diameter.*—2–3 mm.

*Internode length.*—4 cm.

Leaves:

*Arragement.*—Opposite.

*Apex.*—Mucronate.

*Base.*—Oblique.

*Color.*—Upper surface is green (RHS 137A) and lower surface is green (RHS 137B). Venation is yellow-green RHS 145B.

*Margin.*—Entire.

*Size.*—Length is 4.8 cm and width is 2.5 cm, both at full expansion.

*Shape.*—Ovate.

*Texture.*—Coarse.

*Venation.*—Pinnate.

*Pubescence.*—Present, clear.

*Number leaves per stem.*—Leaves occur every 4 cm; the number per stem will vary with the size of the plant.

Flowers:

*Calyx.*—5 sepals; 2 cm×8 mm (length×width); color is green RHS 137B.

*Corolla.*—5 Petals, fused.

*Flower diameter.*—6.0–6.5 cm.

*Fragrant.*—Yes.

*Inflorescence type.*—Solitary.

*Bud.*—1.8 cm in length; 5.0 mm in diameter; color is yellow-green RHS 144C.

*Pistil.*—Compound.

*Ovary.*—Superior, parietal placentation.

*Stamens.*—5 total with two long and three short.

*Peduncle.*—2.7 cm×2 mm (length×width); pubescent.

*Petal color.*—Limbs: upper — white (RHS 155C); lower — white (RHS 155C) with green (RHS 140A) veins. Tube: Inside — yellow-green (RHS 145B) with green (RHS 143C) and purple (RHS 79A) veins; Outside is yellow-green (RHS 145B) with green (RHS 140A) veins.

*Petal apex.*—Reniform.

*Petal margin.*—Smooth.

*Petal pubescence.*—Absent.

*Tube throat diameter.*—6 mm.

*Tube length.*—2.0 cm.

*Pollen color.*—White (RHS 155C).

*Produces seed.*—Yes; <1.0 mm diameter; seed coat with netted pattern; 8,000–10,000 seeds/gram; grey-orange RHS 172B.

Disease and Insect Resistance

No susceptibility to diseases or insects noted to date.

Comparison with Known Cultivars

'Kakegawa S30' is a distinct variety of Petunia owing to its white flower color and creeping, mounding habit. 'Kakegawa S30' is most similar to the variety 'Pink Wave'; however, 'Kakegawa S30' has smaller flowers and a different flower color. Table 1 below shows the characteristics that best distinguish the new variety from the comparison variety.

TABLE 1

| Characteristic | 'Kakegawa S30' | 'Pink Wave' |
|---|---|---|
| Flower diameter | 6.0–6.5 cm | 8.0–8.5 cm |
| Primary petal color (upper) | White RHS 155 C | Rosy pink blush RHS 66A |
| Primary petal color (lower) | White RHS 155 C with light green veins RHS 140A | Rosy pink RHS 68B |

Table 2 below shows 'Kakegawa S30' as compared to the parental varieties.

TABLE 2

| Characteristic | 'Kakegawa S30' | 4UK-1 | P-1a |
|---|---|---|---|
| Flower Color | White | White | Magenta |
| Stem Anthocyanin | Absent | Absent | Present |
| Leaf Shape | Ovate | Ovate | Broad ovate |

I claim:

1. A new and distinct Petunia plant as shown and described herein.

* * * * *